United States Patent
Malek Tabrizi et al.

(10) Patent No.: US 11,065,156 B2
(45) Date of Patent: *Jul. 20, 2021

(54) LENTICULAR LASER INCISION FOR LOW MYOPIA AND/OR HYPEROPIA PATIENTS

(71) Applicant: AMO Development, LLC, Santa Ana, CA (US)

(72) Inventors: Alireza Malek Tabrizi, Fremont, CA (US); Hong Fu, Pleasanton, CA (US); James E. Hill, Santa Ana, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 814 days.

This patent is subject to a terminal disclaimer.

(21) Appl. No.: 15/638,169

(22) Filed: Jun. 29, 2017

(65) Prior Publication Data

US 2018/0000647 A1    Jan. 4, 2018

Related U.S. Application Data

(60) Provisional application No. 62/356,430, filed on Jun. 29, 2016.

(51) Int. Cl.
*A61F 9/008* (2006.01)
*A61B 3/00* (2006.01)

(52) U.S. Cl.
CPC ........ *A61F 9/00827* (2013.01); *A61B 3/0008* (2013.01); *A61F 9/008* (2013.01); *A61F 9/00825* (2013.01); *A61F 2009/0087* (2013.01); *A61F 2009/00872* (2013.01); *A61F 2009/00897* (2013.01)

(58) Field of Classification Search
CPC .. A61F 9/00827; A61F 9/008; A61F 9/00825; A61F 2009/00872; A61F 2009/00897; A61F 2009/0087; A61B 3/0008
See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance, Jr. | |

(Continued)

FOREIGN PATENT DOCUMENTS

WO    2016049442 A1    3/2016

OTHER PUBLICATIONS

Jesper Hjortdal et al., "New Developments in the Lencticule Extraction Procedure", US Ophthalmic Review, 2014;7(1):20-5 DOI: http://doi.org/10.17925/USOR.2014.07.01.20, viewed on May 8, 2020.*

(Continued)

*Primary Examiner* — Allen Porter
*Assistant Examiner* — James Moss
(74) *Attorney, Agent, or Firm* — Johnson & Johnson Surgical Vision, Inc.

(57) ABSTRACT

Embodiments generally relate to ophthalmic laser procedures and, more particularly, to systems and methods for lenticular laser incisions to form a top lenticular incision, a bottom lenticular incision of a lens in the subject's eye, an added shape between the top and bottom incisions where the added shape has no corrective power and a transition ring bisecting both the top and bottom lenticular incisions.

17 Claims, 17 Drawing Sheets

(56) References Cited

U.S. PATENT DOCUMENTS

| | | | |
|---|---|---|---|
| 4,764,930 A | 8/1988 | Bille et al. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,646,791 A | 7/1997 | Glockler | |
| 5,993,438 A | 11/1999 | Juhasz et al. | |
| 6,110,166 A * | 8/2000 | Juhasz | A61F 9/008 128/898 |
| 6,315,413 B1 | 11/2001 | Shimmick et al. | |
| 8,260,024 B2 | 9/2012 | Farrer et al. | |
| 8,394,084 B2 | 3/2013 | Blumenkranz et al. | |
| 8,403,921 B2 | 3/2013 | Blumenkranz et al. | |
| 8,690,862 B2 | 4/2014 | Palanker et al. | |
| 8,709,001 B2 | 4/2014 | Blumenkranz et al. | |
| 10,369,052 B2 * | 8/2019 | Fu | A61F 9/00834 |
| 10,709,611 B2 | 7/2020 | Fu et al. | |
| 2010/0331831 A1 * | 12/2010 | Bischoff | A61F 9/00804 606/5 |
| 2011/0172649 A1 | 7/2011 | Schuele et al. | |
| 2013/0281992 A1 * | 10/2013 | Seiler | A61F 9/00827 606/5 |
| 2014/0081249 A1 * | 3/2014 | Bischoff | A61F 9/00804 606/5 |
| 2014/0104576 A1 | 4/2014 | Bor et al. | |
| 2014/0288540 A1 * | 9/2014 | Bischoff | A61F 9/008 606/5 |
| 2016/0067095 A1 | 3/2016 | Fu et al. | |
| 2016/0089270 A1 | 3/2016 | Fu | |
| 2016/0235586 A1 | 8/2016 | Fu et al. | |
| 2016/0374857 A1 | 12/2016 | Fu et al. | |
| 2017/0143544 A1 * | 5/2017 | Holliday | A61F 9/00827 |
| 2018/0008461 A1 | 1/2018 | Fu et al. | |
| 2020/0069470 A1 | 3/2020 | Fu et al. | |

OTHER PUBLICATIONS

Yu-Chi Liu et al., "Early Corneal Wound Healing and Inflammatory Responses After SMILE: Comparison of the Effects of Different Refractive Corrections and Surgical Experiences", Journal of Refractive Surgery; Thorofare vol. 32, Iss. 5, (May 2016): 346-353. DOI:10.3928/1081597X-20160217-05.*

S. M. Blinder, "Lensmaker's Equation", Wolfram Demonstrations Project, http://demonstrations.wolfram.com/LensmakersEquation/, Published Mar. 7, 2011, viewed on May 8, 2020.*

International Search Report and Written Opinion for Application No. PCT/US2017/040122, dated Sep. 25, 2017, 14 pages.

* cited by examiner

LENTICULAR LASER INCISION FOR LOW MYOPIA AND/OR HYPEROPIA PATIENTS

RELATED APPLICATIONS

This application claims priority to, and the benefit of, under 35 U.S.C. § 119(e) of U.S. Provisional Appl. No. 62/356,430, filed Jun. 29, 2016, which is incorporated herein by reference in its entirety.

FIELD

Embodiments of this invention relate generally to laser-assisted ophthalmic procedures, and more particularly, to systems and methods for lenticular incisions in the cornea for low myopia and/or hyperopia patients.

BACKGROUND

Vision impairments such as myopia (near-sightedness), hyperopia (far-sightedness) and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Hyperopia (far-sightedness) is a visual impairment where light entering the eye does not focus at the retina to produce a sharp image as desired, but rather focuses at a location behind the retina such that a patient sees a blurred disc. The basic principle to treating hyperopia is to add positive focusing power to the cornea. For instance, a hyperopic eye can be treated by placing a convex lens in front of the eye to add a positive focusing power to the eye. After correction, light passing through the convex lens and into the eye focuses at the retina to form a sharp image.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and the OptiMedica Catalys Precision Laser System.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SMILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like.

If part of the cornea is removed, the pressure exerted on the cornea by the aqueous humor in the anterior chamber of the eye will act to close the void created in the cornea, resulting in a reshaped cornea. By properly selecting the size, shape and location of a corneal void, one can obtain the desired shape, and hence, the desired optical properties of the cornea.

In traditional laser surgery treatments, such as LASIK and PRK that correct hyperopia, positive focusing power is added to the cornea by steepening the curvature of the cornea, by for example, removing a ring-shaped stroma material from the cornea. As described earlier, in a LASIK procedure, first, a flap is created, and then, it is lifted so the ring-shaped stroma material can be removed or ablated with an excimer laser. The center of the cornea is not removed while more outward portions of the cornea are removed. The flap is then put back into place. The cornea thus steepens due to the void created in the cornea. Common patterns that steepen the cornea include ring, tunnel and toric shapes. LASIK can typically correct hyperopia for up to 5D (diopter). In a PRK procedure where no flap is created, the epithelium layer is first removed, and the ring-shaped stroma material is then removed by an excimer laser. The epithelium layer will grow back within a few days after the procedure.

More recently, surgeons have started using another surgical technique other than LASIK and PRK for refractive correction. Instead of ablating corneal tissue with an excimer laser following the creation of a corneal flap, the newer SMILE technique involves tissue removal with two femtosecond laser incisions that intersect to create a lenticule for extraction. Lenticular extractions can be performed either with or without the creation of a corneal flap. With the flapless procedure, a refractive lenticule is created in the intact portion of the anterior cornea and removed through a small incision. But, patients with low myopia and/or hyperopia can end up with a relatively small lenticule, which can be difficult to extract.

SUMMARY

Hence, to obviate one or more problems due to limitations and disadvantages of the related art, this disclosure provides improved systems and methods for generating corneal lenticular incisions for correcting low myopia and/or hyperopia using high repetition rate femtosecond lasers. Embodiments of this invention including an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens on the subject's eye. The XY-scan device deflects the pulsed laser beam to form a scan line. The scan line is tangential to the parallels of latitude of the lens. The scan line is then moved along the meridians of longitude of the lens. The top lenticular incision is moved over the top surface of the lens through the apex of the top surface of the lens, and the bottom lenticular incision is moved over the bottom surface of the lens through the apex of bottom surface of the lens.

Other embodiments disclose an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top concave lenticular incision, a bottom concave lenticular incision, and a transition ring incision intersecting both the top and bottom lenticular incisions forming a lens on the subject's corneal stroma.

This summary and the following detailed description are merely exemplary, illustrative, and explanatory, and are not intended to limit, but to provide further explanation of the embodiments as claimed. Additional features and advantages of the embodiments will be set forth in the descriptions that follow, and in part will be apparent from the description, or may be learned by practice of the embodiments. The objectives and other advantages of the embodiments will be realized and attained by the structure particularly pointed out in the written description, claims and the appended drawings.

BRIEF DESCRIPTION OF THE DRAWINGS

The novel features of the embodiments are set forth with particularity in the appended claims. A better understanding of the features and advantages will be facilitated by referring to the following detailed description that sets forth illustrative embodiments, as well as to the accompanying drawings, in which like numerals refer to like parts throughout the different views. Like parts, however, do not always have like reference numerals. Further, the drawings are not drawn to scale, and emphasis has instead been placed on illustrating the principles of the embodiments. All illustrations are intended to convey concepts, where relative sizes, shapes, and other detailed attributes may be illustrated schematically rather than depicted literally or precisely.

DETAILED DESCRIPTION

Embodiments are generally directed to systems and methods for laser-assisted ophthalmic procedures, and more particularly, to systems and methods for lenticular laser incisions for patients with low myopia and/or hyperopia.

Figure 1:
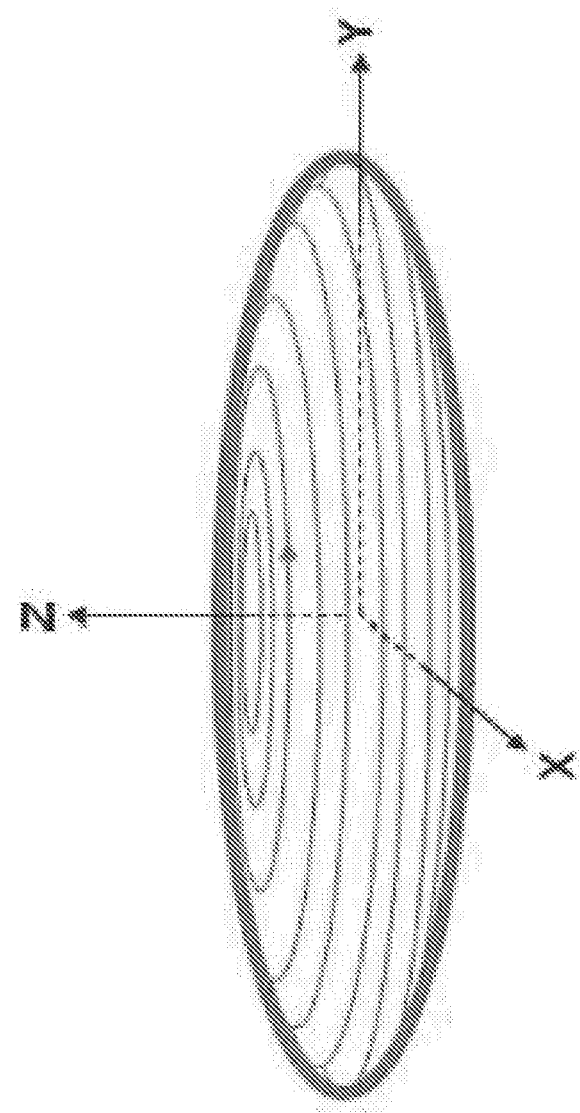
FIG. 1 illustrates a conventional lenticular cut via scanning a single focus spot according to certain embodiments.
Figure 2:
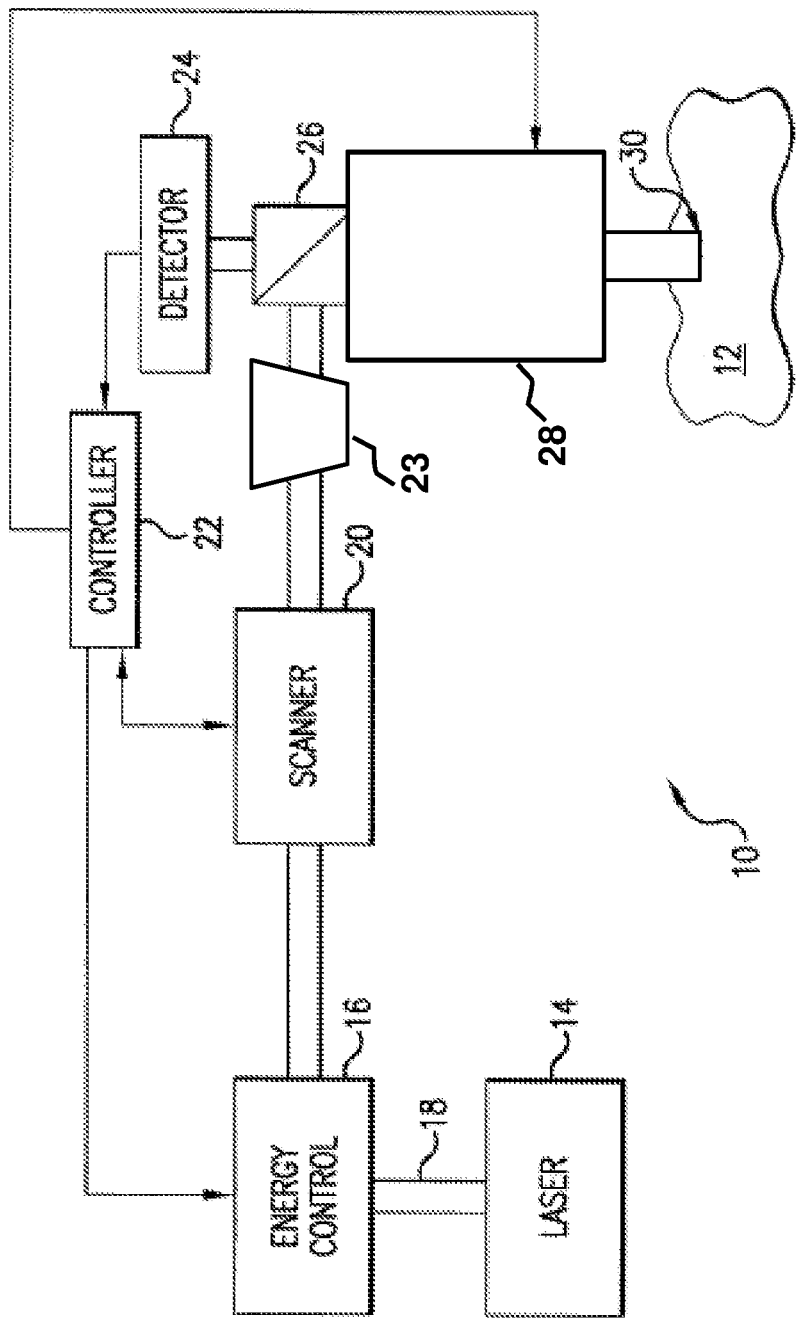
FIG. 2 is a simplified diagram of a surgical ophthalmic laser system according to certain embodiments.

Referring to the drawings, FIG. 2 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, e.g., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photo decomposing one or more intraocular targets within the eye.

Although the laser system 10 may be used to photo alter a variety of materials (e.g., organic, inorganic, or a combination thereof), the laser system 10 is suitable for ophthalmic applications in certain embodiments. In these cases, the focusing optics direct the pulsed laser beam 18 toward an eye (for example, onto or into a cornea) for plasma mediated (for example, non-UV) photo ablation of superficial tissue, or into the stroma of the cornea for intrastromal photo disruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 3:
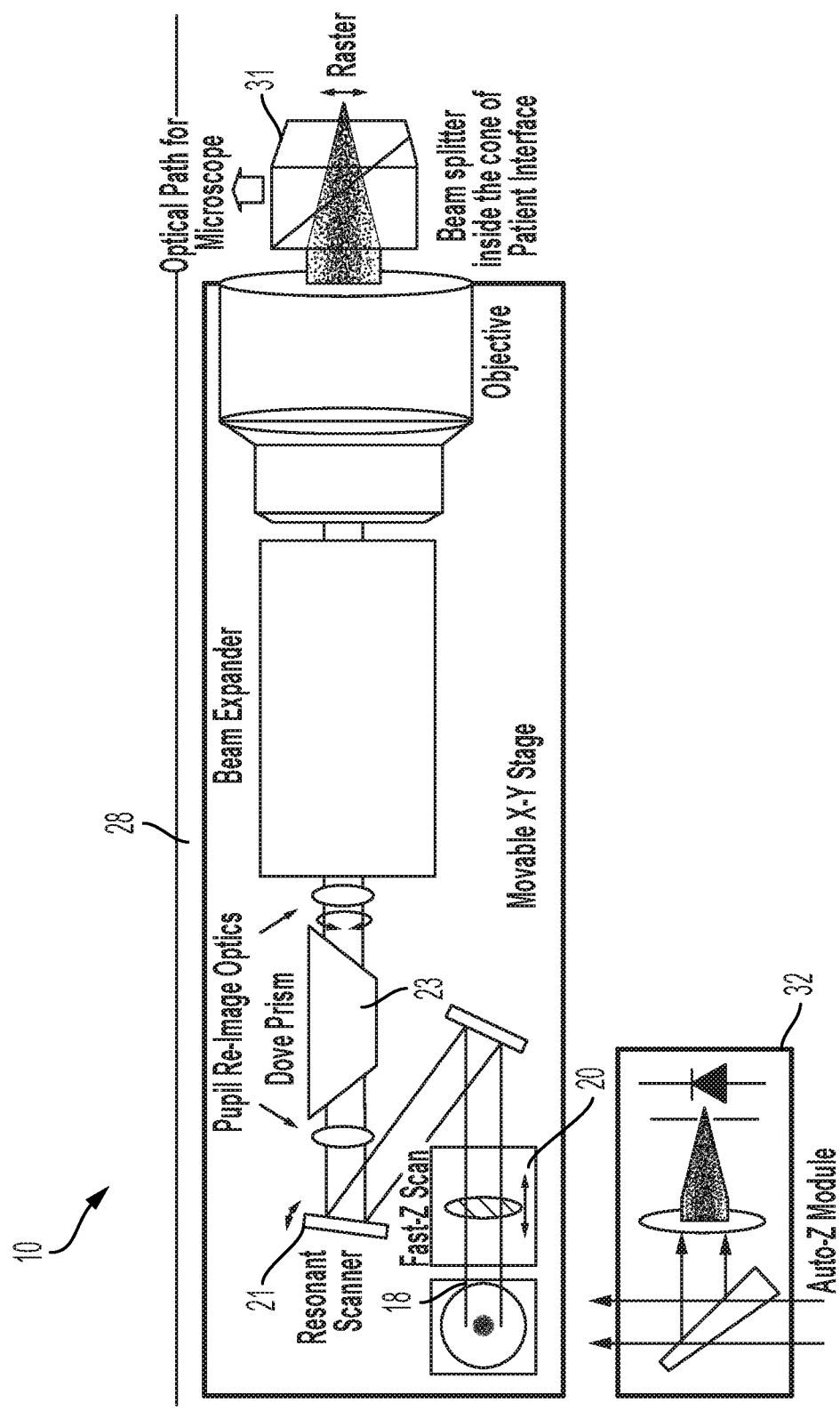
FIG. 3 is another simplified diagram of a surgical ophthalmic laser system according to certain embodiments.

FIG. 3 shows another exemplary diagram of the laser system 10. FIG. 3 shows a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 µm Full Width at Half Maximum (FWHM) focus spot size; and a resonant scanner 21 that produces 1-2 mm scan line with the XY-scanner scanning the resonant scan line to a 10 mm field. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and may reduce the complexity, size, and weight of the laser system. Alternatively, the miniaturized laser system may be designed as a conventional femtosecond laser system, where the patient is treated while lying down.

Figure 4:
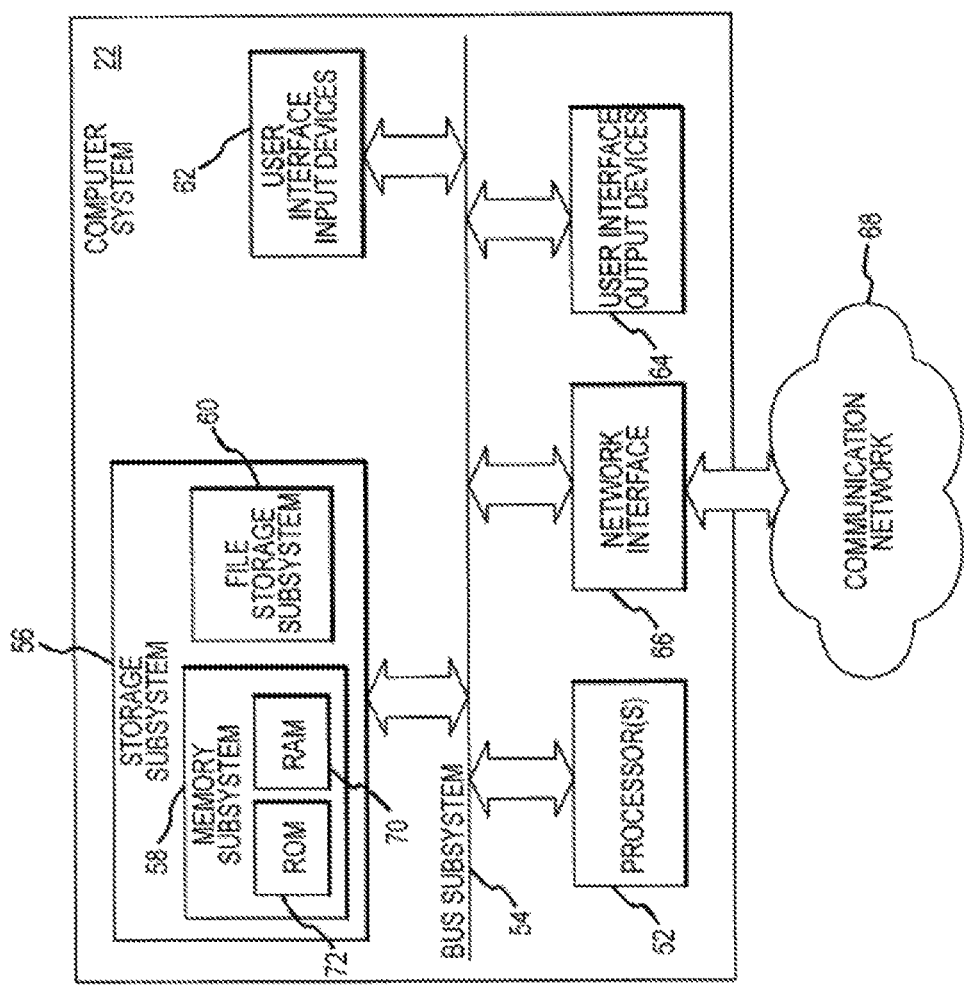
FIG. 4 is a simplified diagram of a controller of a surgical ophthalmic laser system according to certain embodiments.

FIG. 4 illustrates a simplified block diagram of an exemplary controller 22 that may be used by the laser system 10 according to some embodiments. Controller 22 may include at least one processor 52 which may communicate with a number of peripheral devices via a bus subsystem 54. These peripheral devices may include a storage subsystem 56, including a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments. For example, a database and modules implementing the functionality of the methods of the present embodiments, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present embodiments may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 4 is intended only as an example for purposes of illustrating only some embodiments. Many other configurations of controller 22, having more or fewer components than those depicted in FIG. 4, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. patent application Ser. No. 12/987,069, filed Jan. 7, 2011 (published as US20110172649), U.S. patent application Ser. No. 13/798,457 filed Mar. 13, 2013 (published as US20140104576), U.S. patent application Ser. No. 14/848,733, filed Sep. 9, 2015, U.S. patent application Ser. No. 14/865,396, filed Sep. 25, 2015, U.S. patent application Ser. No. 14/968,549, filed Dec. 14, 2015, and U.S. patent application Ser. No. 14/970,898, filed Dec. 16, 2015, which are incorporated herein by reference.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, e.g., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 5:
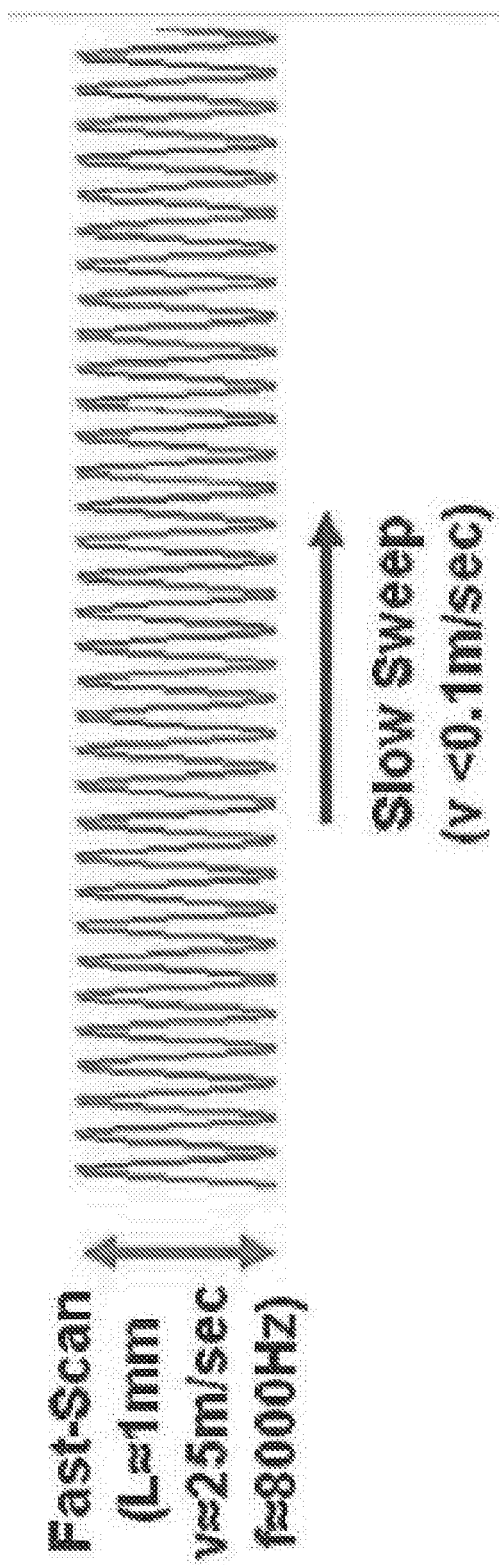
FIG. 5 illustrates an exemplary scanning of a surgical ophthalmic laser system according to certain embodiments.

In some embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner 21 of FIG. 3); second, the fast scan line is slowly swept by much slower X, Y, and Z scan mechanisms. FIG. 5 illustrates a scanning example of a laser system 10 using an 8 kHz resonant scanner 21 to produce a scan line of about 1 mm and a scan speed of about 25 m/sec, and X, Y, and Z scan mechanisms with the scan speed smaller than 0.1 m/sec. The fast scan line may be perpendicular to the optical beam propagation direction, e.g., it is always parallel to the XY plane. The trajectory of the slow sweep can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 6:
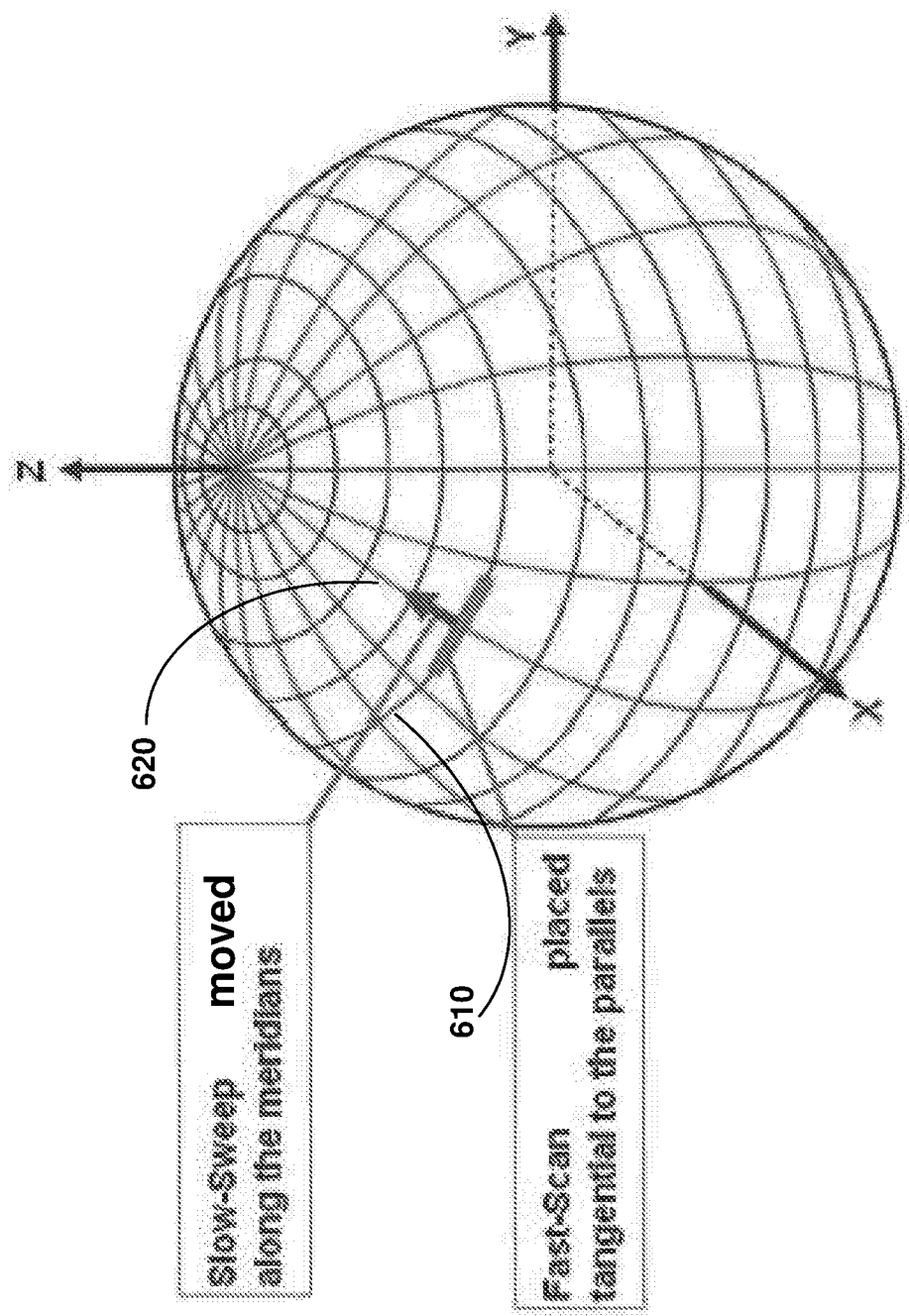
FIG. 6 illustrates an exemplary lenticular incision using a fast-scan-slow-sweep scheme of a surgical ophthalmic laser system according to certain embodiments.

In some embodiments, as shown for example in FIG. 6, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 610. For example, in the miniaturized flap maker laser system 10 of FIG. 3, this can be realized by adjusting a prism 23 to the corresponding orientations via software, e.g., via the controller 22. Second, the slow sweep trajectory preferably moves along the meridians of longitude 620. For example, in the miniaturized flap maker system of FIG. 3, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter (see also FIG. 8). With this preferred procedure, there are no vertical "steps" in the dissection, and vertical side cuts are eliminated. As will be analyzed herein below, the deviations between the laser focus locations and the intended spherical surface dissections are also minimized.

Figure 7:
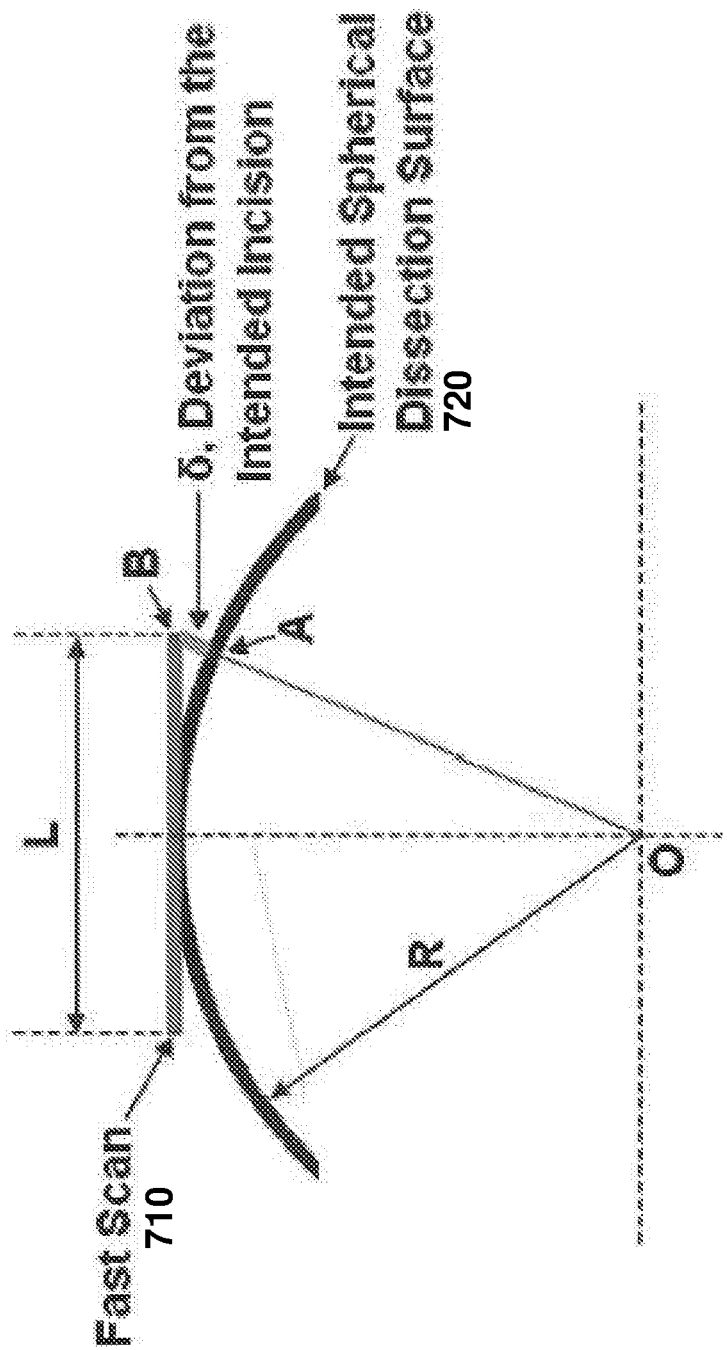
FIG. 7 illustrates a geometric relation between a fast scan line and an intended spherical dissection surface of a surgical ophthalmic laser system according to certain embodiments.

FIG. 7 shows the geometric relation between the fast scan line 710 and the intended spherical dissection surface 720, e.g., of a lens, especially the distance deviation (δ) between the end point B of the scan line 720 and point A on the intended dissection surface 720. The maximum deviation δ is the distance between point A and point B, and is given by $$\delta = \sqrt{R^2 + \frac{L^2}{4}} - R = \frac{L^2}{8R},$$

equation (1), where R is greater than L. R is the radius of curvature of the surface dissection 720, and L is the length of the fast scan.

In an exemplary case of myopic correction, the radius of curvature of the surface dissection may be determined by the amount of correction, ΔD, using the following equation $$\Delta D = \frac{(n-1)}{R_1} + \frac{(n-1)}{R_2},$$

equation (2), where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1$=$R_2$=R (the two dissection surface are equal for them to physically match and be in contact), we have $$R = \frac{2(n-1)}{\Delta D},$$

equation (3).

Figure 8:
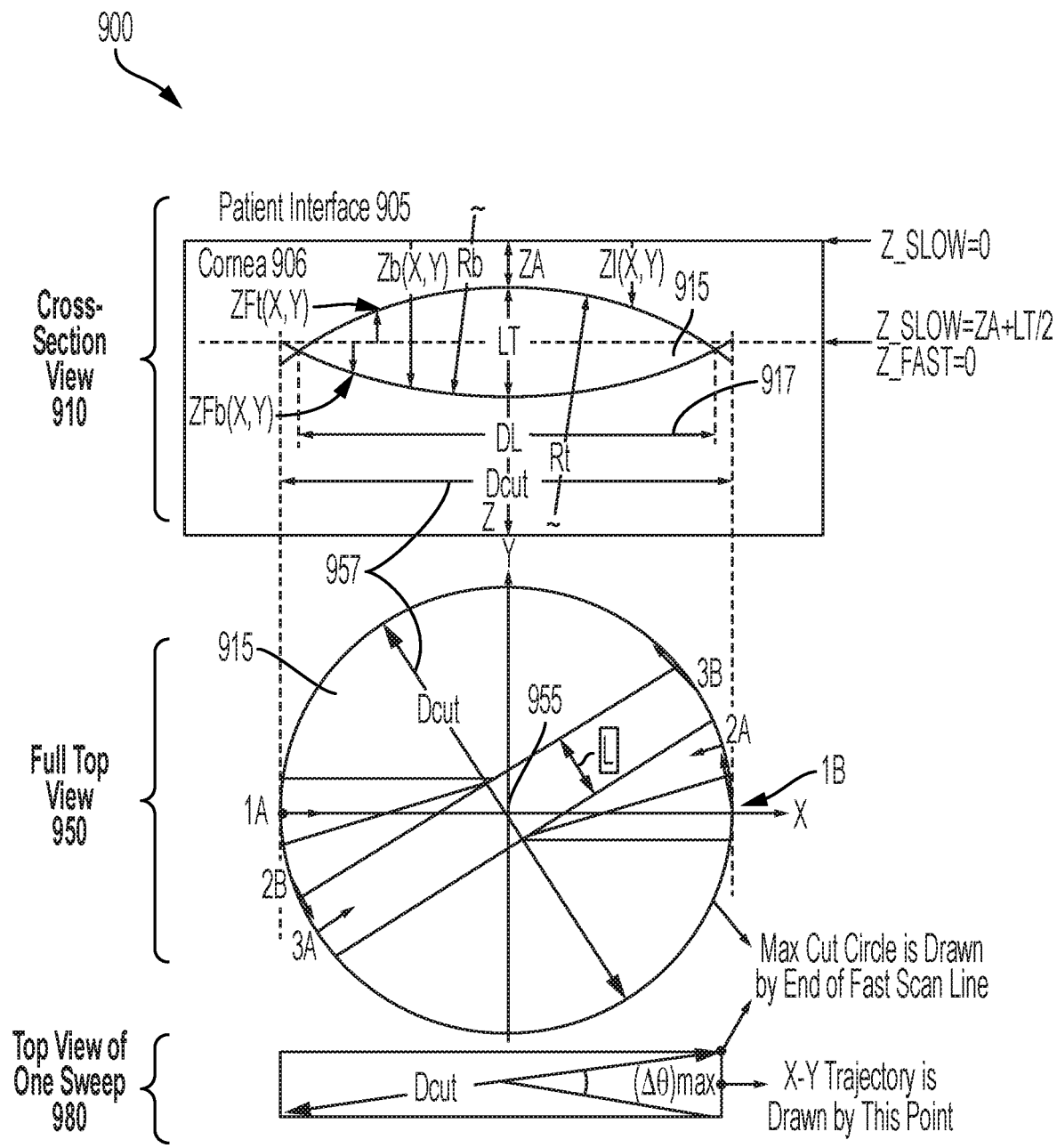
FIG. 8 illustrates an exemplary lenticular incision using a surgical ophthalmic laser system according to certain embodiments.

In an embodiment, FIG. 8 shows an exemplary lenticular incision 900 for extraction using the laser system 10. FIG. 8 shows an exemplary cross-sectional view 910 illustrating a patient interface 905 (or patient interface 31 as shown in FIG. 3), cornea 906, and lenticular incision volume 915, which will be referred herein as lens to be extracted. Rt and Rb are the radii of curvature for the top surface and bottom surface of a lenticular incision, respectively. ZFt (Zt) is the depth of the top surface of the lenticular incision. ZFb (Zb) is the depth of the bottom surface of the lenticular incision. The Z depths may be calculated based on the respective radii. LT is the lens thickness at the lens apex, or center thickness of the lens. ZA is depth of the lens apex. DL is the diameter of the lenticular incision, or the lens. {Z_SLOW=0} is the Z reference position before the laser system 10 calculates and sets Z_SLOW, e.g., {Z_SLOW=ZA+LT/2} the center depth of the lens, which remains fixed for the duration of the incision procedure. Z_SLOW may then be the reference position for the Z-scanner for top and bottom incision surfaces. In an embodiment, the diameter of the lens may be received from an operator of the laser system 10, or may be calculated by the laser system 10. The thickness of the lens may be determined, for example, by the total amount of correction (e.g., diopter) and the diameter of the lens.

A top view 950 of the lenticular incision 900 illustrates three exemplary sweeps (1A to 1B), (2A to 2B) and (3A to 3B), with each sweep going through (e.g., going over) the lenticular incision apex 955. The incision, or cut, diameter 957 ($D_{CUT}$) should be equal to or greater than the to-be-extracted lenticular incision diameter 917 (DL). A top view 980 shows the top view of one exemplary sweep. In some embodiments, the lenticular incision may be performed in the following steps:

1. Calculate the radius of curvature based on the amount of correction, e.g., a myopic correction.
2. Select the diameter for the lenticular incision to be extracted.
3. Perform the side incision first (not shown) to provide a vent for gas that can be produced in the lenticular surface dissections. This is also the incision for the entry of forceps and for lens extraction.
4. Perform bottom surface dissection (the lower dissection as shown in cross-sectional view 910). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on, until the full bottom dissection surface is generated.
5. Perform the top surface dissection (the upper dissection as shown in the cross-sectional view 910) in a similar manner as the bottom dissection is done. It is noted that the bottom dissection is done first. Otherwise, the bubble generated during the top dissection will block the laser beam in making the bottom dissection.

For illustrative purposes, in a myopic correction of ΔD=10 diopter (e.g., 1/m), using equation (3), R=75.2 mm, which is indeed much greater than the length L of the fast scan. Assuming a reasonable scan line length of L=1 mm, using equation (1), the deviation δ≈1.7 μm. This deviation is thus very small. For comparison purpose, the depth of focus of a one micron (FWHM) spot size at 1 μm wavelength is about ±3 μm, meaning the length of focus is greater than the deviation δ.

Figure 9:
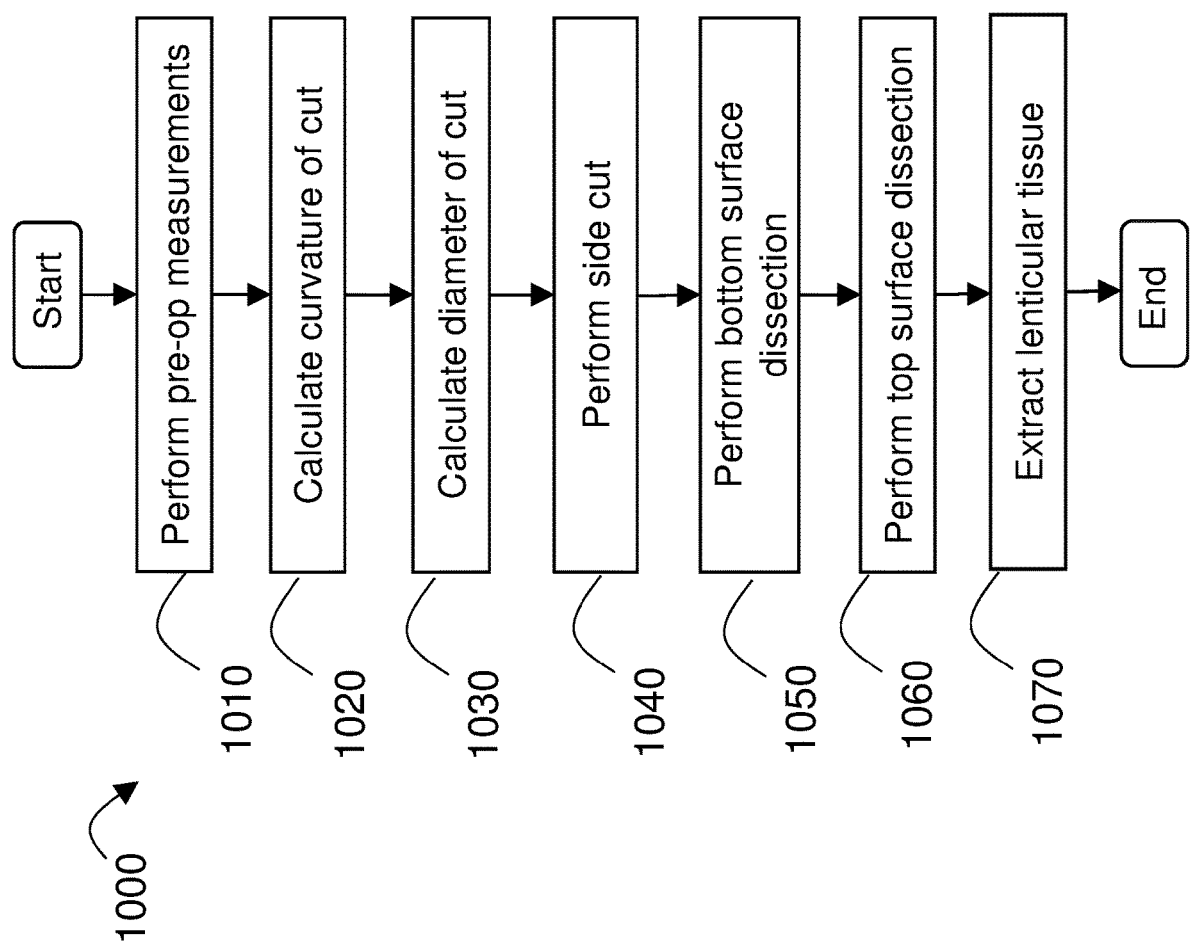
FIG. 9 is a flowchart illustrating a process according to certain embodiments.

FIG. 9 illustrates a process 1000 of the laser system 10 according to an embodiment. The laser system 10 may start a surgical procedure performing pre-operation measurements 1010. For example, in an ophthalmologic surgery for myopic correction, the myopic diopter is determined, the SLOW_Z position is determined, and so on. The laser system 10 calculates the radius of curvature based on the amount of correction, e.g., the myopic correction determined in pre-operation measurements (Action Block 1020), as shown, for example, in equations (2) and (3) above. The laser system 10 calculates the diameter of the incision 1030, as shown by $D_{CUT}$ in FIG. 8. $D_{CUT}$ is equal to or greater than the diameter of the to-be-extracted lenticule (DL in FIG. 8). The laser system 10 first performs side incision to provide a vent for gas that can be produced in the lenticular surface dissections, and for tissue extraction later on 1040. The laser system 10 then performs the bottom lenticular surface dissection 1050 before performing the top lenticular surface dissection 1060. The lenticular tissue is then extracted 1070.

In other embodiments, the laser system 10 may also be used to produce other three-dimensional surface shapes, including toric surfaces for correcting hyperopia and astigmatism. The laser system 10 may also be used for laser material processing and micromachining for other transparent materials. Correction of hyperopia by the laser system 10 is discussed in detail below.

Figure 10:
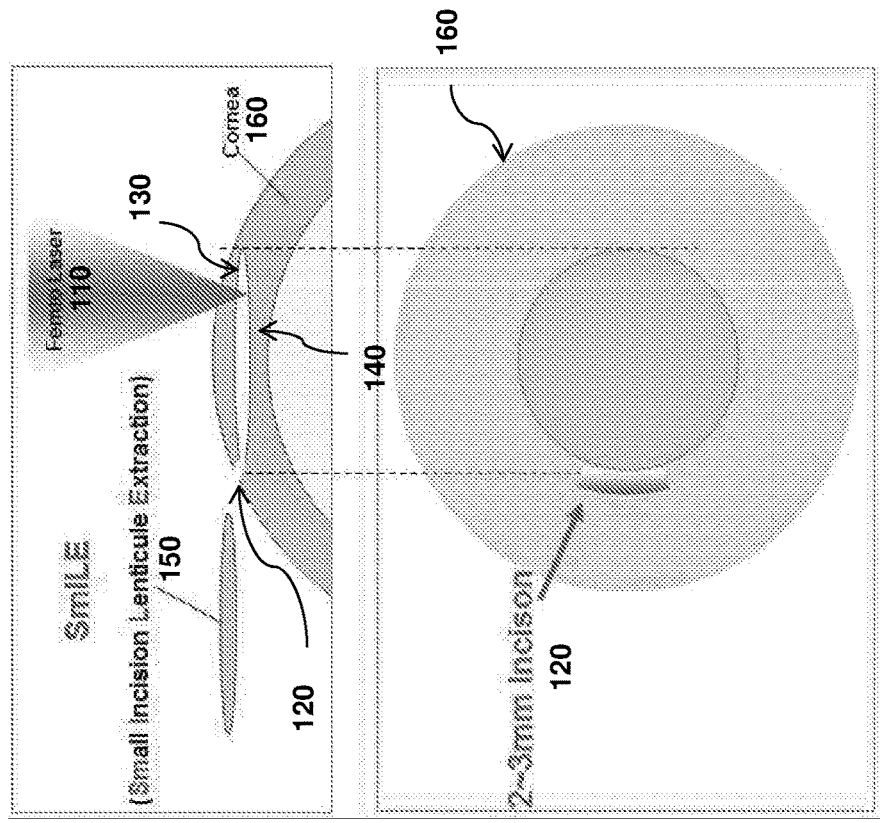
FIG. 10 illustrates an exemplary Small Incision Lenticule Extraction procedure according to certain embodiments.

In the SMILE procedure illustrated in FIG. 10, a femtosecond laser 110 is used to make a side cut 120, an upper or top surface cut 130 and a lower or bottom surface cut 140 that forms a cut lens or lenticule 150. A tweezer, for example, may then be used to extract the cut lens beneath the anterior surface of the cornea 160 through the side cut 120. SMILE may be applied to treat myopia and/or hyperopia by cutting and extracting a convex lens-shaped stroma material with a femtosecond laser. However, SMILE techniques have not been applied in treating hyperopia.

Low Myopic/Hyperopic Correction Examples

In certain treatment examples, a patient may only need a minor refractive correction for low-power myopia (e.g. −0.5 diopters (D) to −4.0 D) or low-power hyperopia (+2.0 D). The systems and methods described here using high reprate (MHz range) femtosecond lasers may be used to incise precise concave incisions within the corneal tissue and create a correction for the patient. But with minor corrections the concave cuts may be shallow and the thickness of the resulting lenticular tissue small. And a small lenticule may be difficult to extract especially if the lenticular tissue is pulled through an extraction cut.

Systems and methods here may be used to widen the gap between the upper and lower lenticular cuts making the lenticular tissue for extraction thicker and easier to remove. In some examples, a 50 μm lenticule thickness may ease lenticule extraction. The systems and methods can achieve this while maintaining the refractive correction necessary for the patient and also maintaining an appropriately sized diameter cut.

Figure 11A:
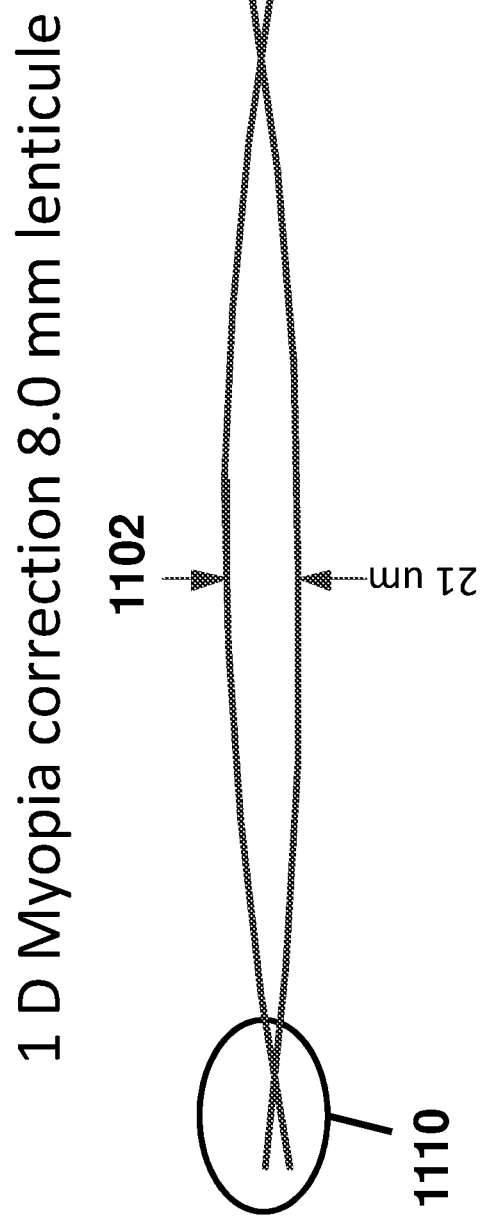
FIG. 11A illustrates an exemplary side view of two lenticular incisions according to certain embodiments.

FIG. 11A shows a side view illustration of two example lenticular incisions in a cornea used to make the required power correction in the eye as described herein. In this example, the patient had a low myopia and/or hyperopia correction.

Low myopia (or hyperopia) corrections may require a shallower curve to the top and bottom lenticular incisions than incisions used to correct a high myopia (or hyperopia). Such shallowly angled incisions for the top and bottom surfaces of the lenticular incisions may result in a very thin lenticular tissue 1102 only 21 μm thick, in this example, with different corrections resulting in different thicknesses.

Because the corneal stroma is curved and the eye is only so large, it may be desirable to limit the diameter of any intrastromal incision to ensure the integrity of the eye after treatment. For example, the diameter of the lenticule in FIG. 11A is between 5 and 9 mm, for example 8.0 mm wide. As discussed above, in order to facilitate removal of the lenticular tissue between the top and bottom surface incisions, the incisions for the top and bottom lenticular surfaces may overlap slightly at the edges 1110. Such an overlap may help ensure that there is no tissue bridging with the cornea and incised lenticule which is to be extracted. And because extraction may be from any method including by pulling the incised lenticule out of an extraction cut with a forceps, it may be difficult pulling a thin lenticule out of the extraction cut without tearing the thin lenticular tissue.

Figure 11B:
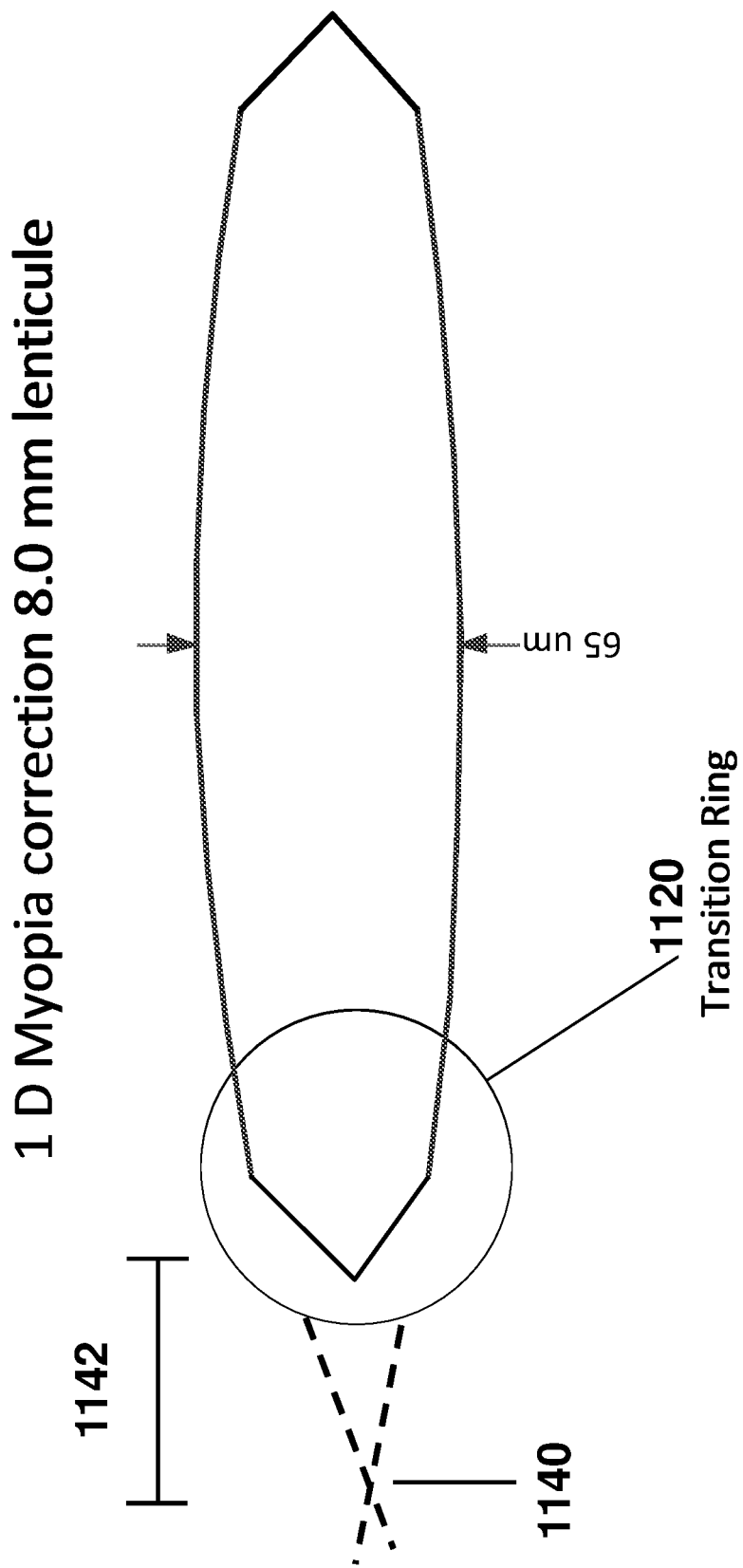
FIG. 11B illustrates an exemplary side view of two lenticular incisions and a transition ring according to certain embodiments.

FIG. 11B shows a side view illustration of two example lenticular incisions used in some embodiments described here, but this time, the two lenticular incisions are spaced wider apart and there is a transition ring 1120. Again, this example shows an 8.0 mm diameter lenticule but with the incisions spaced wider apart, here 65 µm as an example. As the curved lenticular incisions affect the correction of the eye, and not the amount of corneal tissue removed, the overall thickness of the lenticular tissue is irrelevant in terms of refractive correction. Thus, by spacing the two lenticular cuts apart, the same correction may be made with a resulting thicker lenticular tissue. This thicker tissue may be easier to extract.

It is clear that by incising the top and bottom lenticular incisions with a wider space between them, the overall lenticular tissue would also need to be larger in diameter 1142 if the curvature of the incisions remained constant. In the example of FIG. 11B, dashed lines show where the two wider spaced lenticular incisions would overlap 1140 if they continued at the same curvature angle as they did in the example of FIG. 11A. But in the example of FIG. 11B, the diameter of the lenticular tissue is the same as in FIG. 11A, 8.0 mm. Thus, to get the lenticular tissue diameter to remain at 8 mm, and thereby make the top and bottom incisions to overlap at 8 mm, a transition ring 1120 may be cut. The transition ring 1120 may be cut to join the top and bottom incisions at a different curvature angle in order to change the diameter 1142 of the lenticule had it otherwise not been incised.

By incising this transition ring around the circumference of the lenticular tissue, the same correction lenticular cuts may be made and the same diameter of the lenticular tissue may be incised as described in FIG. 11A, but the result would be a thicker lenticule that may be easier to remove. Such a transition ring may encompass the lenticule and provide >50 µm lenticule thickness along with the required separation of the lenticule from the cornea, and also a smooth transition from lenticule top surface to bottom surface.

Such a transition ring 1120, with a steeper curvature angle, may also result in a cleaner lenticule edge which may make extraction easier. Such relatively steeper cuts may result in less tissue bridging than shallower cuts. It should be noted that the transition ring 1120 could be incised at any angle and form any diameter lenticule, so long as the top and bottom lenticular incisions are made for the proper refractive correction and so long as the lenticule effectively covered the pupil and refracted the light entering the pupil. The transition ring 1120, as viewed from the side as shown in FIG. 11B, could be a straight incision to join the top and bottom incisions, or it could be angled or curved as shown in FIG. 11B. Any kind of curvature may be incised by the lasers as described above.

It should be noted that the transition ring 1120 may be incised, even in cases where the top and bottom lenticular incisions do actually meet or even overlap. A transition ring 1120 may be useful to clean up an edge or make extraction easier, even in cases where the top and bottom incisions are not spaced farther apart. Because the transition ring can be any depth and take any form of curvature, it can be tailored to the needs of individual patients.

Figure 12:
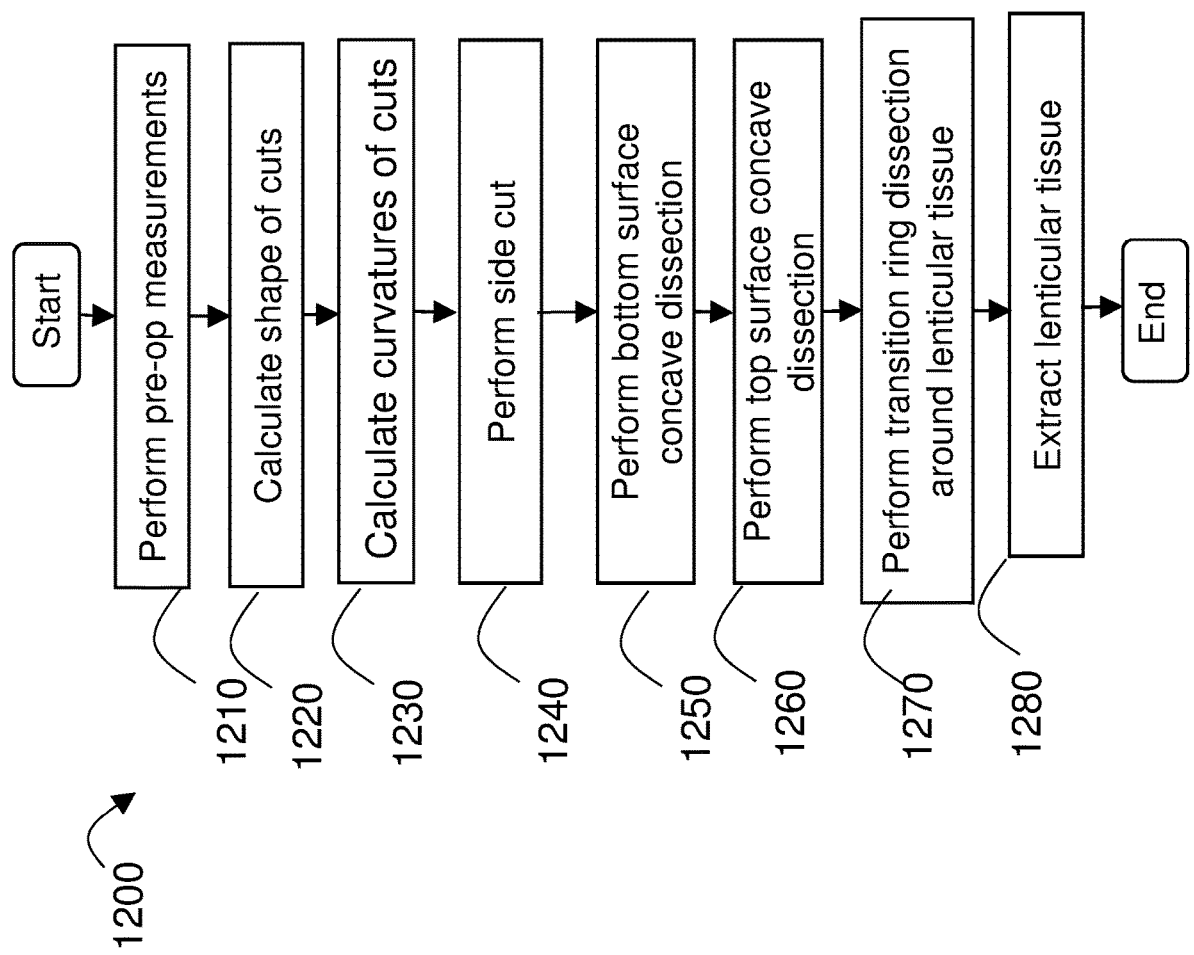
FIG. 12 is a flowchart illustrating an exemplary surgery process according to certain embodiments.

FIG. 12 is a flowchart illustrating an exemplary surgery process 1200 according to some embodiments here. The laser system 10 may start a surgical procedure performing pre-operation measurements 1210. For example, in an ophthalmologic surgery for hyperopic correction, the hyperopic diopter is determined, the SLOW_Z position is determined, and so on. The laser system 10 calculates the shape of the incisions 1220. The laser system 10 calculates the radius of curvatures based on the amount of correction, e.g., the hyperopic correction determined in pre-operation measurements 1230, as determined by Equations (4)-(8), for example. The laser system 10 first performs a side incision to provide a vent for gas that can be produced in the lenticular surface dissections, and for tissue extraction later on 1240. The laser system 10 then performs the bottom lenticular surface dissection 1250 before performing the top lenticular surface dissection 1260. Performing the dissections in this order allows gas to vent out of the cornea instead of becoming trapped in gas bubbles within the cornea. This order also prevents having to traverse the focal point of the laser beam through incised tissue. It should be noted that in the embodiments described here, these bottom surface 1250 and top surface 1260 would not necessarily meet or touch. In other words, the edges of the top and bottom cuts may have a space in between. Next, a transition ring cut is made around the circumference of the lenticular tissue 1270. This transition ring, depending on the space between the edges of the top and bottom incisions, may then join the two incisions and create a lenticule. The lenticular tissue may then be extracted from the side cut.

Figure 13:
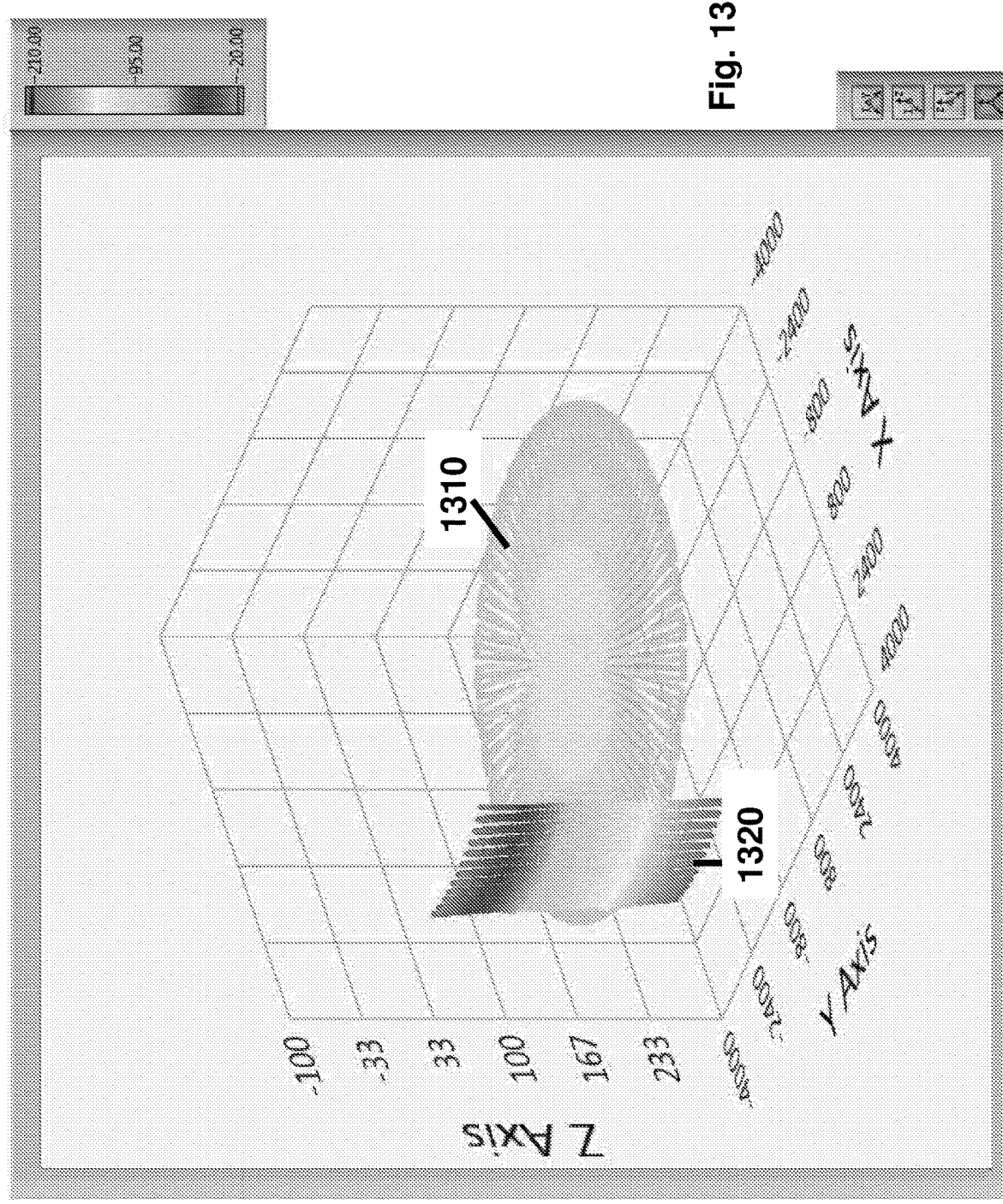
FIG. 13 illustrates an exemplary perspective view of cuts used to form and extract lenticular tissue according to certain embodiments.

FIG. 13 shows an example perspective of a lenticular tissue after the two main incisions 1310, which are designed to make the required power correction in the eye. In the example, the cornea itself is not shown, but the outline of the lenticule 1310 and side cut 1320 only. The top and bottom cut surfaces may overlap to facilitate separation of the lenticule from the eye. In this example, the correction is low so the resulting lenticular tissue is thin, only a few µm. As discussed above, extracting a thin lenticular tissue may be difficult and may result in collateral damage and tearing. The other incision is the side extraction incision 1320.

Figure 14:
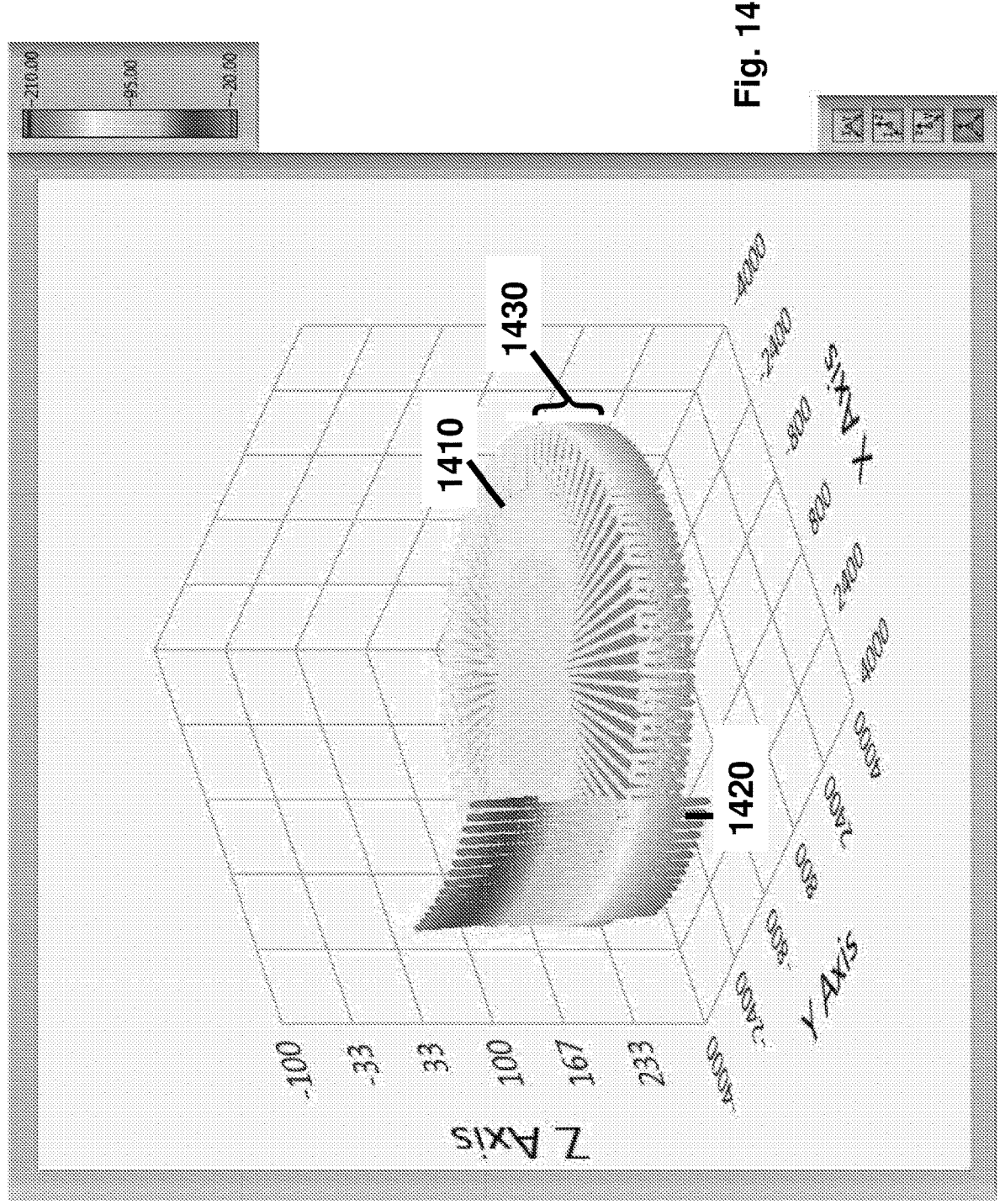
FIG. 14 illustrates an exemplary perspective view of cuts used to form and extract lenticular tissue with a transition ring according to certain embodiments.

FIG. 14 shows an example perspective of a lenticular tissue after the two main incisions 1410, which are designed to make the required power correction in the eye. Again, the cornea is not shown but the lenticule outline is shown 1410 along with the side cut 1420. In this example, the correction is low but the two concave surfaces have been spaced farther apart 1430 than in FIG. 13. In addition, in order to keep the diameter of the lenticular tissue at a certain diameter, there is a transition incision 1430 forming a transition ring around the circumference of the lenticular tissue 1430. The result is a thicker lenticular tissue with the same correction, same diameter but easier to extract.

It should be noted that the methods disclosed here can be used to produce other three dimensional surface shapes such as hyperopic correction. These methods can be applied to material processing for any transparent or semi-transparent medium or tissue.

Added Shape Examples

In some examples, when a lenticule correction is calculated, the resultant material is relatively thin as compared to the corneal thickness. This may occur in low myopia or low hyperopia patients for example where the correction is between 0.5 and 3 diopters (D). But a thin lenticule may be difficult to extract from a cornea after it is incised by the laser as described above. Thin lenticules may tear, rip, come apart or otherwise fall to pieces resulting in trouble for an operating surgeon. Another reason an added shape may need to be added to a lenticule is because a thin incision for low hyperopia and/or myopia may be too thin for a femtosecond laser as described herein. In using a femtosecond laser, the cutting limit for a low hyperopia and/or myopia lenticule may be below the threshold that the waist of the femtosecond laser beam may incise.

Therefore, there is a need to add a thickness to the calculated thin lenticule in order to facilitate extraction. Referring again to FIG. 12, such an added shape would cause the calculations of the curvature cuts 1230 to be spaced further apart, causing a specifically calculated space between the bottom surface cut 1250 and the top surface cut 1260.

But such an added thickness should not substantially change the calculated corrective lenticule shape calculated to correct the hyperopia and/or myopia. In other words, the added shape should have substantially no power of correction. Additionally, such a calculation is complicated by the procedure which may use a physical docking patient interface for the laser system. Such a physical patient interface may deform the eye when docked or applanated. And adding a layer of uniform thickness to the calculated lenticule under applanation will introduce a refractive error that can be a significant part of the low target correction, for example 0.5D of 2Ds correction. Thus, the shape of the added material must be customized for the correction.

Figure 15:
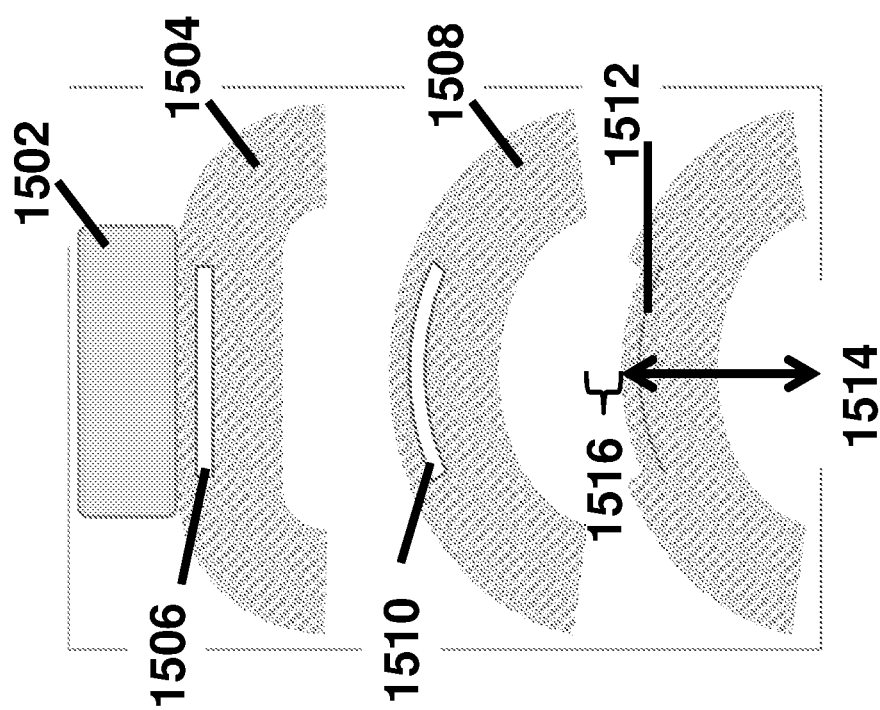
FIG. 15 illustrates exemplary views of corneas and lenticules according to certain embodiments.

FIG. 15 shows an example of these complications. First, FIG. 15 shows a patient interface 1502 docked on a cornea 1504. An example lenticule is shown 1506 cut in the cornea 1504. Also shown is the cornea 1508 in a natural, undocked position. It is clear that when the cornea returns to its natural position 1508, the lenticule 1510 has a different shape than it did when it was incised 1506.

Next, FIG. 15 also shows the end result of the procedure 1512 where the resultant corneal curvature is reduced from Rc 1514 to (Rc−δ) and the focal distance is reduced by δ 1516. This can also induce a myopic error, and may be factored into the lenticule calculations.

Therefore, the size and shape of the non-corrective added shape to the corrective top and bottom lenticular incisions, must be determined and incised so that when the cornea is allowed to assume its natural shape, the added shape adds no corrective power to the corrective lenticule. Embodiments here may be used to calculate and incise such a shape to add to a corrective top and bottom lenticule calculations. This added shape may be the same for hyperopic and myopic patients.

Figure 16:
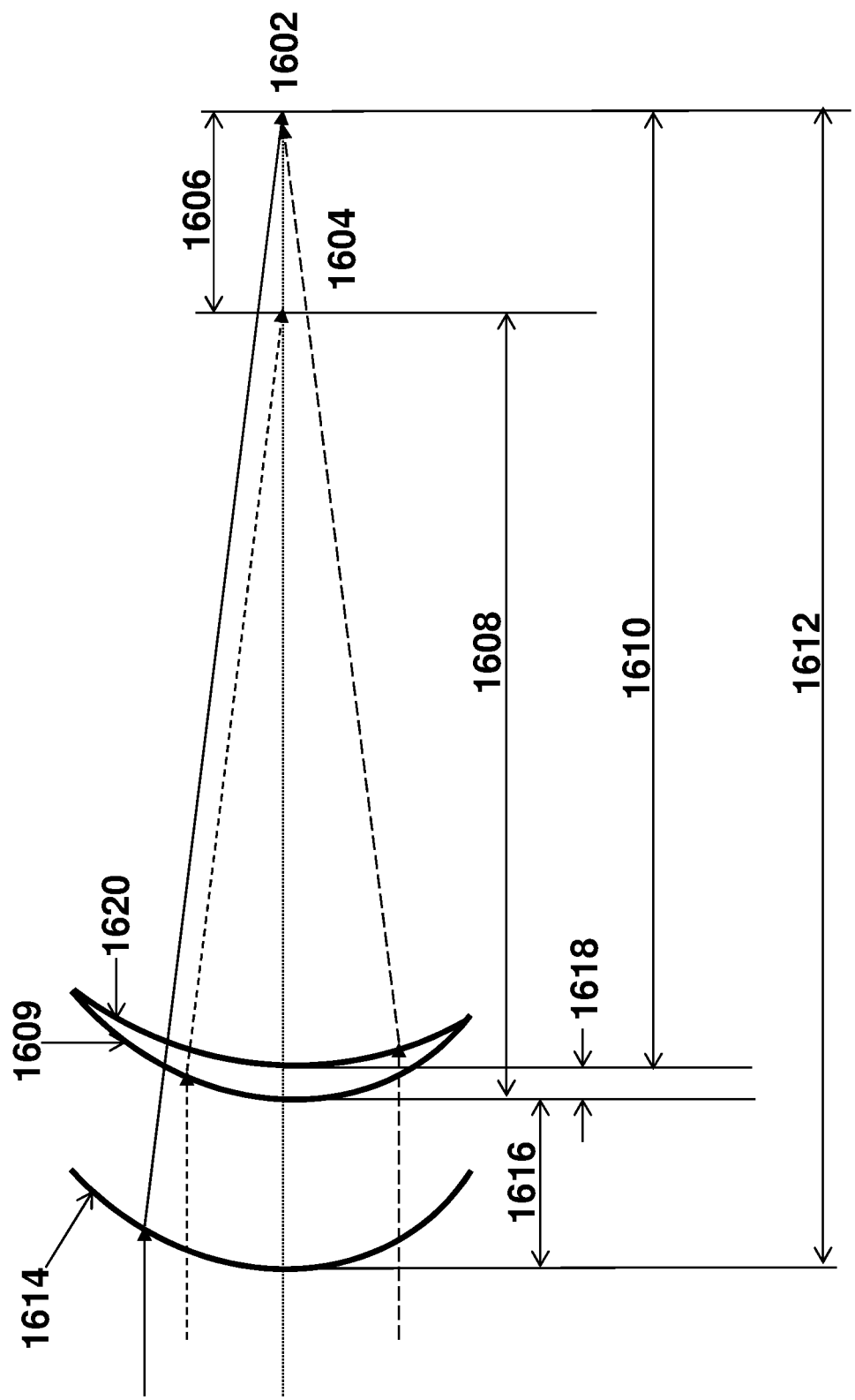
FIG. 16 illustrates exemplary diagrams of calculations of added lenticule thickness according to certain embodiments.

FIG. 16 shows a diagram of how such an added thickness may be calculated. In the diagram, the target focal plane 1602 is shown. The defocus after the fixed thickness is removed 1604 is also shown. The distance between these points is an error ε 1606. The focal length fo 1608 after removing a fixed thickness 1609 is shown along with the focal length fe 1610 of the target focal plane 1602 after removing the fixed thickness Δ2 1618. As is the focal length fc 1612 of the corrected curvature after removing the first lenticule Rc 1614. The distance the focal length was reduced δ 1616 is shown. The lenticule thickness Δ2 1618 is shown. The new lenticule curvature Re to correct the added thickness 1620 is shown, where the total added thickness Δa=δ+Δ2. Further, where $n_c$ is the index of medium, which is the cornea in this case.

$$f = \frac{R \cdot n_c}{n_c - 1}$$

$$R_0 = R_c - \delta$$

$$f_0 = \frac{(R_c - \delta) \cdot n_c}{n_c - 1}$$

$$f_e = f_c - (\delta + \Delta_2)$$

$$\varepsilon = f_c - \delta - f_0 = \frac{\delta}{n_c - 1}$$

$$R_e = R_c - \frac{(n_c - 1)}{n_c} \cdot (\delta + \Delta_2)$$

Where f is focal length. Where fc is original connected focal length. Where R is radius of curvature. Where Ro is new surface if you just remove δ. Where Rc is radius of curvature if primary correction but cannot be removed. Where 6 is additional thickness that will induce error. The total added thickness Δa=δ+Δ2 consists of two parts, a uniform thickness part δ and a lenticule part with thickness Δ2. Thus, using these calculations, the added thickness Δa can be calculated to increase the size of the lenticule, while not changing the corrective power of it, even accounting for the applanated cornea during procedure.

CONCLUSION

All patents and patent applications cited herein are hereby incorporated by reference in their entirety.

The use of the terms "a" and "an" and "the" and similar referents in the context of describing some embodiments (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate some embodiments and does not pose a limitation on the scope of some embodiments unless otherwise claimed. No language in the specification should be construed as indicating any non-claimed element as essential to the practice of the embodiments.

While certain illustrated embodiments of this disclosure have been shown and described in an exemplary form with a certain degree of particularity, those skilled in the art will understand that the embodiments are provided by way of example only, and that various variations can be made without departing from the spirit or scope of the embodiments. Thus, it is intended that this disclosure cover all modifications, alternative constructions, changes, substitutions, variations, as well as the combinations and arrangements of parts, structures, and steps that come within the spirit and scope of the embodiments as generally expressed by the following claims and their equivalents.

What is claimed is:

1. A method for creating lenticular incisions to correct low myopic/hyperopic patients using an ophthalmic surgical laser system, the method comprising:
- placing a patient interface device in contact with a cornea of a patient's eye to applanate the cornea;
- generating a pulsed femtosecond laser beam;
- delivering the pulsed femtosecond laser beam into a stroma of the cornea;
- deflecting, by an XY-scan device, the pulsed laser beam;
- modifying, by a Z-scan device, a depth of a focus of the pulsed laser beam; and
- calculating, by a controller, an initial top lenticular shape, an initial bottom lenticular shape, wherein the initial top lenticular shape and the initial bottom lenticular shape define an initial space between them, and a shape of an added space, wherein the initial top lenticular shape and the initial bottom lenticular shape are calculated based on a predetermined correction power, wherein the shape of the added space has a uniform thickness part with a uniform first thickness and a lenticular part with a second thickness at its center, wherein the second thickness is calculated based on a shape difference between the applanated cornea and the cornea in an unapplanated state, and wherein the shape of the added space introduces zero correction power in the cornea in the unapplanated state;
- calculating, by the controller, a top lenticular incision shape based on the initial top lenticular shape and the shape of the added space, and a bottom lenticular incision shape based on the initial bottom lenticular shape and the shape of the added space;
- controlling, by a controller, the XY-scan device and the Z-scan device to form an incised lenticule in the cornea, by incising, while the cornea is applanated by the patient interface device:
  - a top lenticular incision in the stroma of the cornea, having the calculated top lenticular incision shape and a circumferential periphery;
  - a bottom lenticular incision in the stroma of the cornea, symmetric to the top lenticular incision, having the calculated bottom lenticular incision shape and a circumferential periphery; and
  - a transition ring or side cut incision intersecting the circumferential periphery of the top lenticular incision and the circumferential periphery of the bottom lenticular incision; and
- removing the patient interface device from the cornea.

2. The method of claim 1 wherein the shape of the added space is calculated based on the predetermined correction power.

3. The method of claim 1 wherein the incised lenticule is at least 40 μm thick at its center.

4. The method of claim 3 wherein low hyperopic/myopic patients are 0.5 diopters to 3.0 diopters.

5. The method of claim 1 wherein the transition ring incision has a top edge and a bottom edge, and the top edge and the bottom edge have the same circumference.

6. The method of claim 5 wherein the transition ring has a middle edge between the top edge and bottom edge and the middle edge has a larger circumference then the top edge circumference and the bottom edge circumference.

7. The method of claim 5 wherein the transition ring has a middle edge between the top edge and bottom edge and the middle edge has a same circumference as the top edge circumference and the bottom edge circumference.

8. The method of claim 1 wherein the transition ring has a diameter of between 5 and 9 mm.

9. The method of claim 1 wherein the transition ring is 8 mm in diameter.

10. An ophthalmic surgical laser system to correct low hyperopia and/or myopia, comprising:
- a laser delivery system for delivering a femtosecond laser beam into a cornea of an eye;
- an XY-scan device to deflect the laser beam laterally;
- a Z-scan device to modify a depth of a focus of the laser beam; and
- a controller configured to calculate an initial top lenticular shape, an initial bottom lenticular shape, wherein the initial top lenticular shape and the initial bottom lenticular shape define an initial space between them, and a shape of an added space, wherein the initial top lenticular shape and the initial bottom lenticular shape are calculated based on a predetermined correction power, wherein the shape of the added space has a uniform thickness part with a uniform first thickness and a lenticular part with a second thickness at its center, wherein the second thickness is calculated based on a shape difference between the cornea in an applanated state and the cornea in an unapplanated state, and wherein the shape of the added space introduces zero correction power in the cornea in the unapplanated state, and to further calculate a top lenticular incision shape based on the initial top lenticular shape and the shape of the added space, and a bottom lenticular incision shape based on the initial bottom lenticular shape and the shape of the added space;
- wherein the controller is further configured to control the XY-scan device and the Z-scan device to form an incised lenticule in a corneal stroma with the laser beam including incising, while the cornea is applanated by a patient interface device:
  - a top lenticular incision having the calculated top lenticular incision shape and a circumference;
  - a bottom lenticular incision symmetric to the top lenticular incision having the calculated bottom lenticular incision shape and a circumference; and
  - a transition ring incision intersecting both the top lenticular incision circumference and the bottom lenticular incision circumference.

11. The system of claim 10 wherein the shape of the added space is calculated based on the predetermined correction power.

12. The system of claim 10 wherein a distance between the top lenticular incision and the bottom lenticular incision, as measured from their centers, is at least 40 μm.

13. The system of claim 10 wherein the transition ring has a top circumference edge and a bottom circumference edge, and the top circumference edge and the bottom circumference edge have the same circumference.

14. The system of claim 13 wherein the transition ring has a middle circumference edge between the top circumference edge and bottom circumference edge and the middle circumference edge is larger than the top circumference edge and the bottom circumference edge.

15. The system of claim 13 wherein the transition ring has a middle circumference edge between the top circumference edge and bottom circumference edge and the middle circumference edge is the same as the top circumference edge and the bottom circumference edge.

16. The system of claim 10 wherein the transition ring has a diameter of between 5 and 9 mm.

17. The system of claim 10 wherein the transition ring is 8 mm in diameter.

\* \* \* \* \*